(12) United States Patent
Iida et al.

(10) Patent No.: US 7,458,969 B2
(45) Date of Patent: Dec. 2, 2008

(54) THERAPEUTIC DEVICE FOR TISSUE FROM LIVING BODY

(75) Inventors: Koji Iida, Sagamihara (JP); Norihiko Hareyama, Hino (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/140,084

(22) Filed: May 6, 2002

(65) Prior Publication Data
US 2003/0208201 A1 Nov. 6, 2003

(51) Int. Cl.
*A61B 18/04* (2006.01)
(52) U.S. Cl. .......................... 606/27; 606/41
(58) Field of Classification Search ............. 606/41–52, 606/205, 27–31
See application file for complete search history.

(56) References Cited

U.S. PATENT DOCUMENTS

| | | | |
|---|---|---|---|
| 4,219,025 A | 8/1980 | Johnson | 128/303.1 |
| 4,231,371 A | 11/1980 | Lipp | 128/303.1 |
| 5,308,311 A | 5/1994 | Eggers et al. | 606/28 |
| 5,451,224 A * | 9/1995 | Goble et al. | 606/48 |
| 5,593,406 A | 1/1997 | Eggers et al. | 606/29 |
| 5,716,366 A * | 2/1998 | Yates | 606/139 |
| 5,792,137 A * | 8/1998 | Carr et al. | 606/29 |
| 5,810,811 A * | 9/1998 | Yates et al. | 606/50 |
| 6,602,252 B2 * | 8/2003 | Mollenauer | 606/46 |

FOREIGN PATENT DOCUMENTS

| | | |
|---|---|---|
| DE | 8809437.5 | 11/1988 |
| JP | 6-7366 | 1/1994 |
| JP | 10504485 | 5/1998 |
| JP | 2000210296 | 8/2000 |

OTHER PUBLICATIONS

Japanese Laid Open Publication No. 2000-254135 dated Sep. 19, 2002, English Translation not available.
Japanese Laid Open Publication No. 6-217987 dated Aug. 9, 1994, English Translation not available.
Japanese Laid Open Publication No. 8-103449 dated Apr. 23, 1996, English Translation not available.
Japanese Laid Open Publication No. 6-030946 dated Feb. 8, 1994, English Translation not available.

* cited by examiner

*Primary Examiner*—Michael Peffley
*Assistant Examiner*—Aaron Roane
(74) *Attorney, Agent, or Firm*—Ostrolenk, Faber, Gerb & Soffen, LLP

(57) ABSTRACT

The therapeutic device for treating a living tissue, has jaws and serving as a pair of openable/closable holding portions each having a distal end portion configured to hold the living tissue, and a heating plate provided on at least one of the jaws and, and used to treat the living tissue, wherein a plurality of heat generating mechanism provided independently controllable are provided on the heating plate.

24 Claims, 13 Drawing Sheets

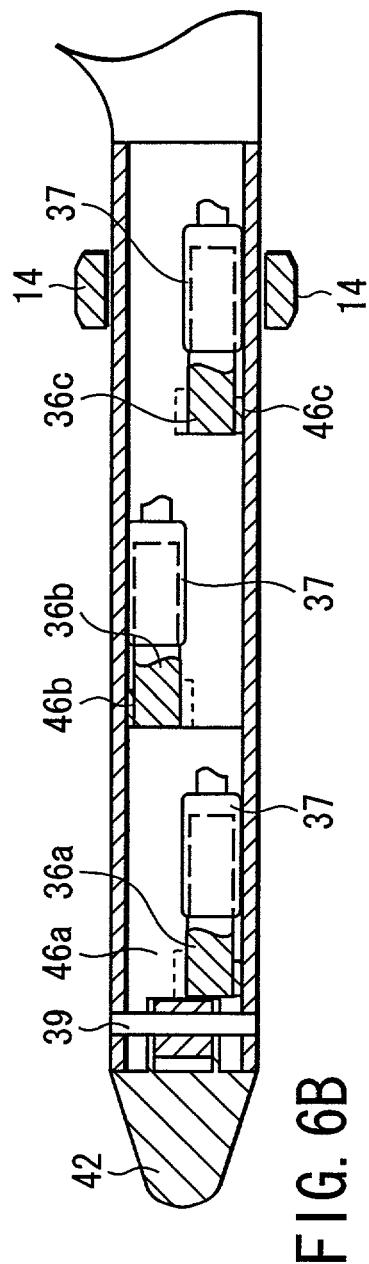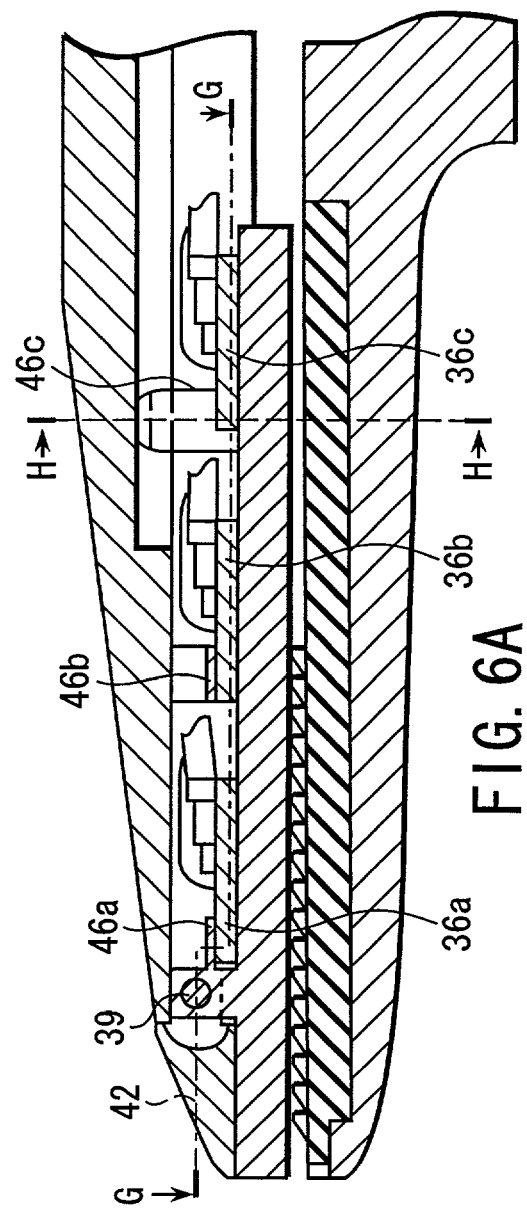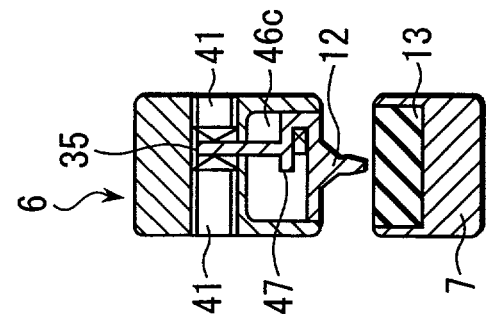

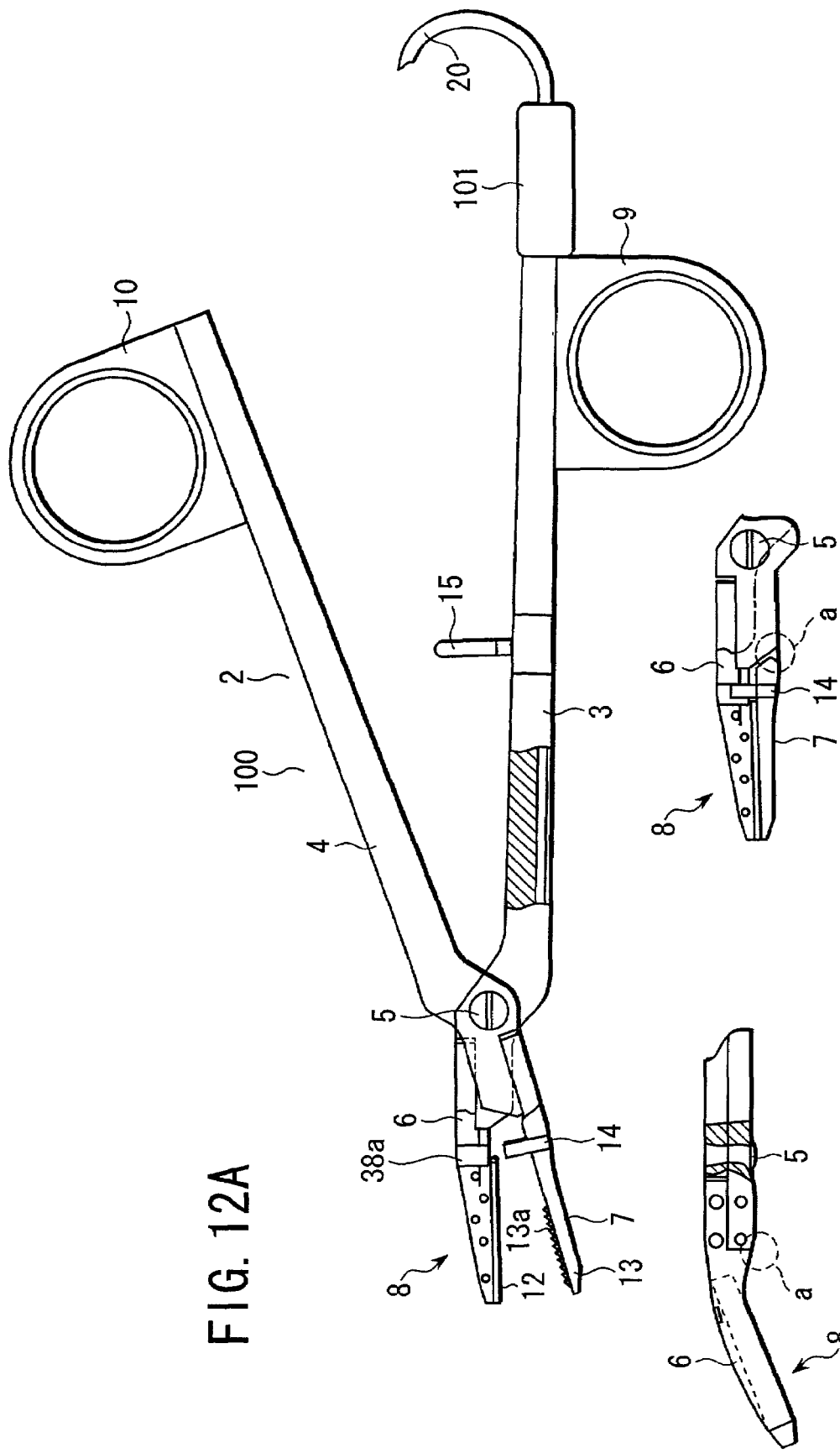

THERAPEUTIC DEVICE FOR TISSUE FROM LIVING BODY

BACKGROUND OF THE INVENTION

1. Field of the Invention

The present invention relates to a therapeutic device for treating a tissue of a living body, by holding, coagulating and cutting the tissue.

2. Description of the Related Art

Conventionally-known living tissue therapeutic devices generally include a pair of holding members for holding a tissue of a living body, in which a heat generator is provided on one or both sides of the holding members and the heat generator is turned on to generate heat while holding a tissue so as to coagulate the tissue or cut the coagulated portion. The tissue treatment devices of this type are used for various cases, such as hemostasis of a blood vessel contained in a living tissue, cauterization of a diseased portion or bleeding point on a surface layer of a living tissue, and blockage of the oviduct for the purpose of contraception. A living tissue therapeutic device is used to stop bleeding from a blood vessel or block the oviduct, and can coagulate a tissue of a living body of the patient that needs to be treated. Further, the coagulated living tissue can be cut with the therapeutic device.

For example, U.S. Pat. No. 5,792,137 discloses a treatment device including a silicon semiconductor serving as a heat generator having a sharp female cutting edge at the holding section of the holding forceps, and with this device, electricity is applied to the silicon semiconductor to generate heat due to its resistance, so as to coagulate the tissue of a living body and cut it.

U.S. Pat. No. 4,219,025 and U.S. Pat. No. 4,231,371 each disclose a technique in which a plurality of heater elements are provided on a cutting blade made of an electrical insulating material, and these heater elements are constructed separate from each other so that they can be controlled independently, thus making it possible to keep the temperature of the cutting edge constant.

U.S. Pat. No. 5,593,406 discloses a treatment device including a hook-shaped resistance heating portion provided at the distal end portion of the insertion section, and with this device, a tissue from a living body is cut while heating it.

U.S. Pat. No. 5,308,311 discloses a treatment device including a sharp female cutting blade provided at the distal end portion, and a heating element provided on a side surface of the female cutting blade, and with this device, a tissue from a living body is cut while coagulating it with the side surface.

Jpn. Pat. Appln. KOKAI Publication No. 6-7366 and German Utility Model Application G8809437 each disclose holder forceps provided with an adjustable stopper mechanism at the handle portion; however they are not of a type equipped with a heat generator at the holder portion for holding a living tissue for coagulating and cutting the tissue.

However, with the technique disclosed in U.S. Pat. No. 5,792,137, described above, an uneven distribution of temperature results because it contains only one heat generator. More specifically, usually, heat generators which generate heat by way of electrical resistance have positive temperature coefficients. In other words, when the temperature increases, the electrical resistance increases, whereas when the temperature decreases, the electrical resistance decreases. With this structure, if a living tissue is held by a part of the heat generating portion, the temperature of the portion which is in contact with the tissue decreases, and therefore the electric resistance partially decreases. The calorific value is determined by R×I×I (R is resistance and I is current), and therefore the calorific value of the portion in contact with the living tissue decreases, and the temperature of that portion decreases. Here, even if the output is increased attempting to compensate for this, the temperature of the portion in contact with the living tissue will not increase, but only the other portion, which is not in contact with the tissue, heats up. As a result, an uneven distribution of temperature is created, and therefore it requires much time to coagulate and cut the tissue.

Further, the heat generator is bonded to the holder portion in its entire surface, and therefore, with this bonding method, a large contact surface is involved. As a result, there is a drawback of heat being radiated as it is propagated to the holder portion. Further, since the contact surface is made of a metal and therefore is hard, if there is even a slight gap between holding pieces when they are closed, the tissue cannot be accurately treated (especially it cannot be properly cut).

Further, U.S. Pat. No. 4,219,025 and U.S. Pat. No. 4,231,371 are directed to a structure in which the cutting edge is on one side, and hemostasis and coagulation are carried out by lightly pressing the device onto a living tissue; therefore such a technique of treating a living tissue while holding it is not considered in these documents. This structure also entails the problem of the coagulation force being weak.

Furthermore, U.S. Pat. No. 5,308,311 is also directed to a structure in which the cutting edge is on one side, and hemostasis and coagulation are carried out by lightly pressing the device to a living tissue; therefore such a technique of treating a living tissue while holding it is not considered in this document. This structure also entails the problem of requiring much time to coagulate a living tissue.

BRIEF SUMMARY OF THE INVENTION

The object of the present invention is to provide a therapeutic device which can prevent an uneven distribution of temperature in its holder portion, and can cut a tissue from a living body, while coagulating it, quickly and accurately, thereby making it possible to shorten the time of the operation.

According to the present invention, there is provided a therapeutic device for treating a living tissue, comprising: a pair of holding portions openable/closable, configured to hold the living tissue, at a distal end portion of the device; and a heating portion provided on at least one of the holding portions and configured to treat the tissue, wherein a plurality of independently controllable heat generating means are provided for the heating portion.

With the above-described structure, the heating members serving as a plurality of heating means can be independently controlled by the power device each to a respective set heating temperature. Thus, when the calorific value at the section of the heating portion that is in contact with the living tissue is decreased and accordingly the temperature of the section is lowered, the resistance value of the means is detected and the output to the heating member is increased. In this manner, the uneven temperature distribution of the heat generating portions can be prevented, thereby making it possible to perform coagulation and cutting of the tissue quickly and accurately.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 6A is a longitudinal section view of the distal end portion of a thermal-coagulating cutting forceps according to the third embodiment of the present invention;

FIG. 6B is a cross sectional view of the forceps taken along the line G-G in FIG. 6A;

FIG. 6C is a cross sectional view of the forceps taken along the line H-H in FIG. 6A;

FIG. 12A is a side view of a therapeutic device for a living tissue, according to the ninth embodiment of the present invention;

FIG. 12B is a top view of the distal end of the device of this embodiment;

FIG. 12C is a side view of the distal end portion thereof while it is closed;

DETAILED DESCRIPTION OF THE INVENTION

Figure 1B:
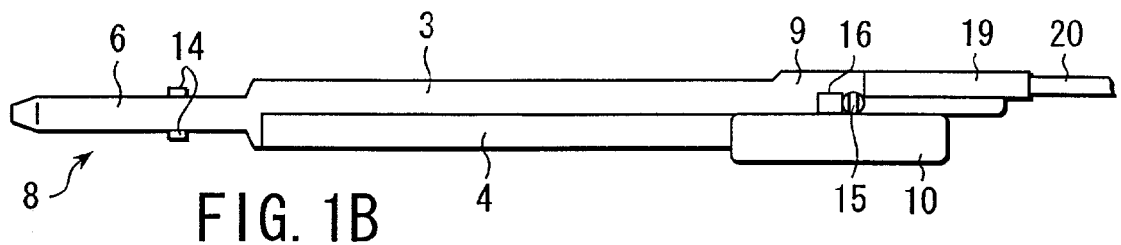
FIG. 1B is a top view of the forceps shown in FIG. 1A.
Figure 1A:
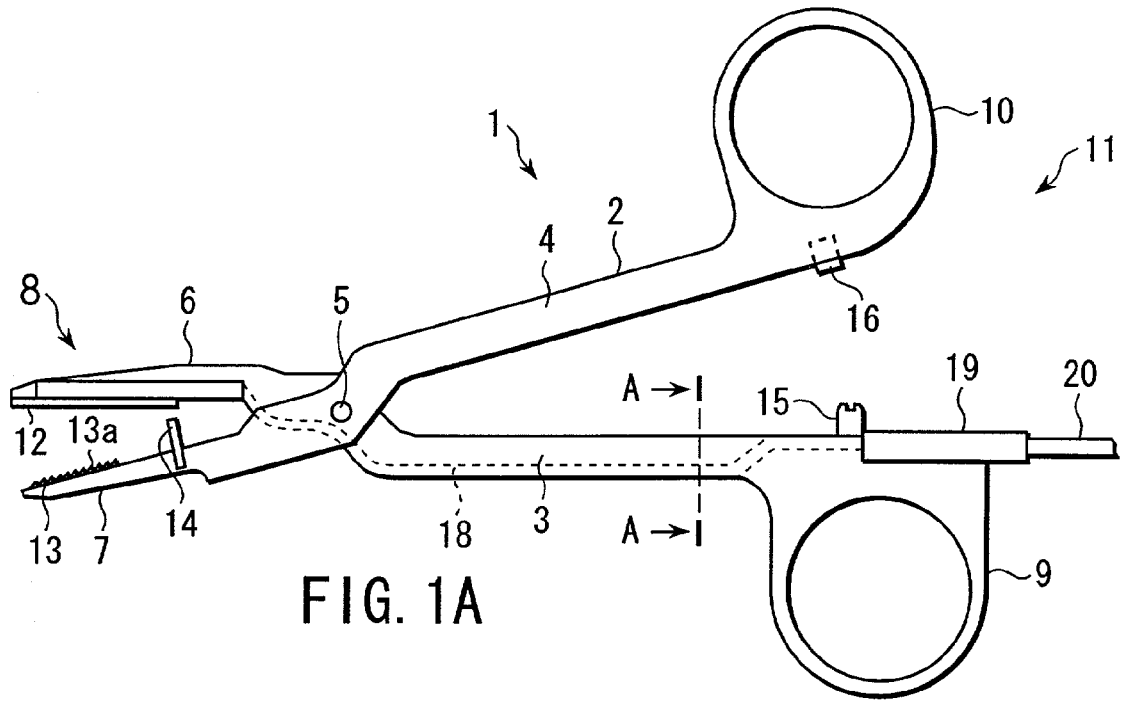
FIG. 1A is a side view of a thermal-coagulating cutting forceps according to the first embodiment of the present invention, while the distal end portions are opened.
Figure 1C:
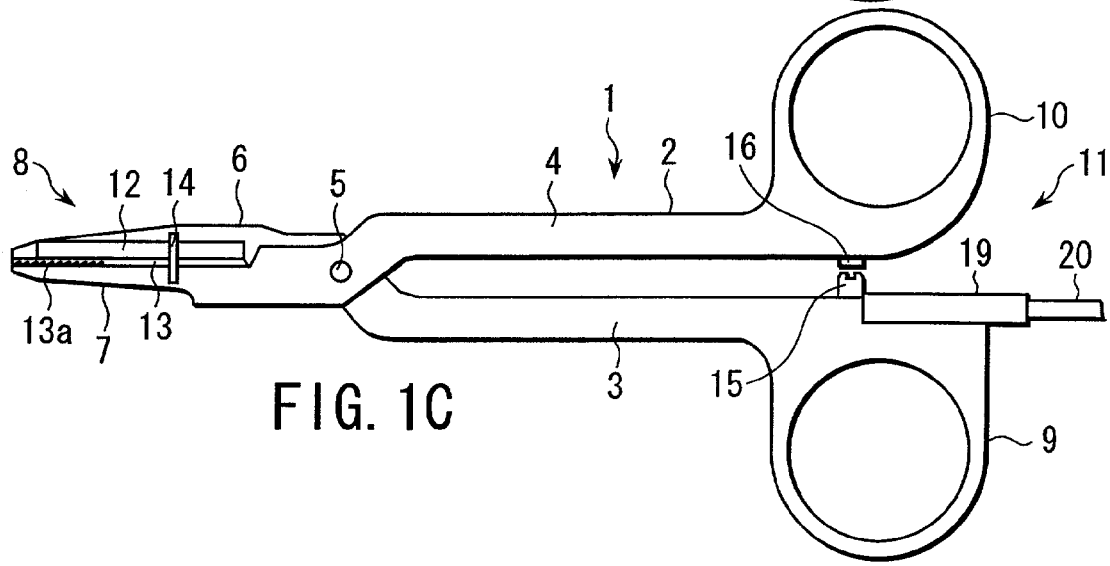
FIG. 1C is a side view of the forceps while the distal end portions are closed.
Figure 1D:
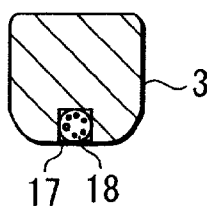
FIG. 1D is a cross sectional view of the forceps taken along the line A-A in FIG. 1A.
Figure 2A:
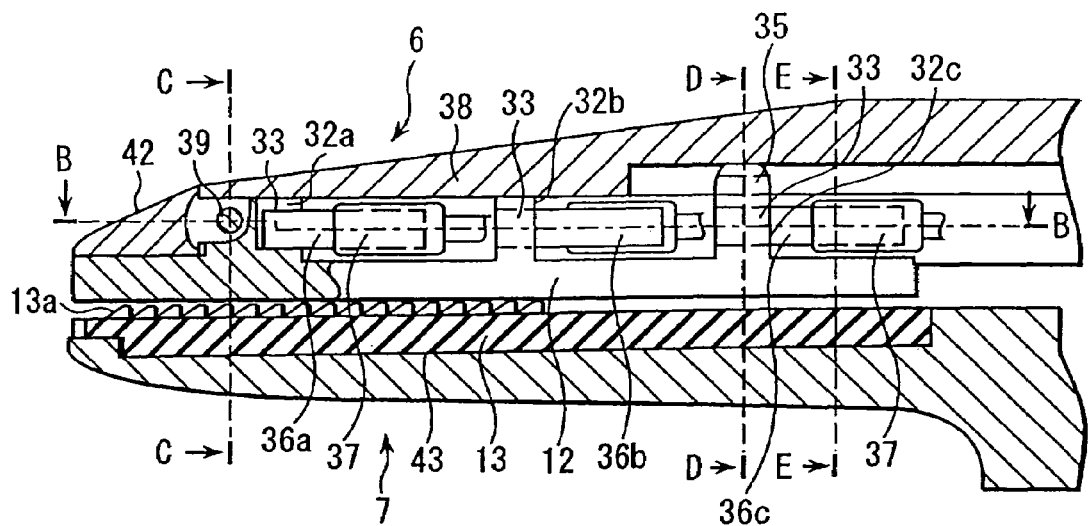
FIG. 2A is a longitudinal sectional view of the distal end of this embodiment.
Figure 2B:
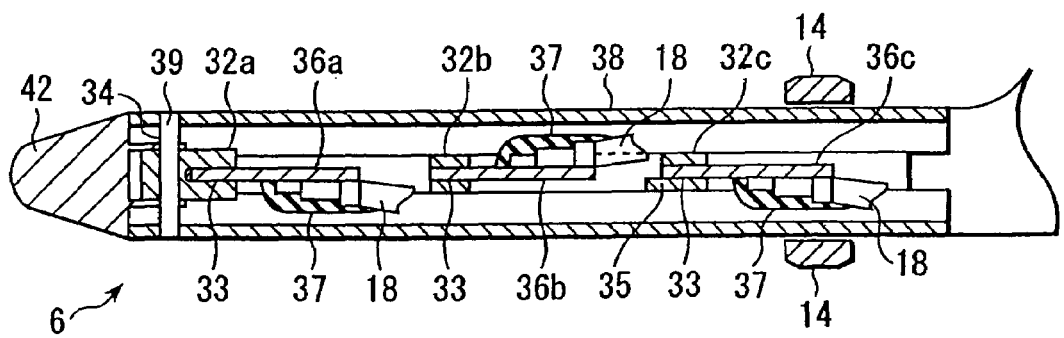
FIG. 2B is a cross sectional view of the forceps taken along the line B-B in FIG. 2A.
Figure 3A:
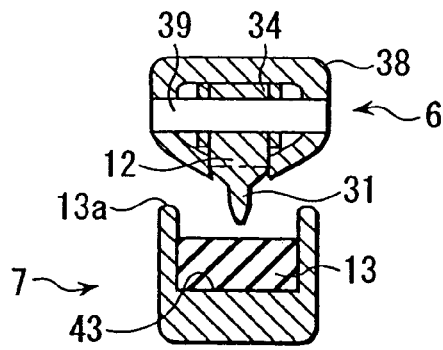
FIG. 3A is a cross sectional view of the forceps taken along the line C-C in FIG. 2A.
Figure 3B:
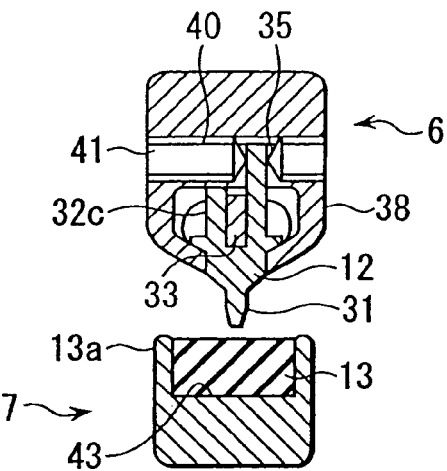
FIG. 3B is a cross sectional view of the forceps taken along the line D-D in FIG. 2A.
Figure 3C:
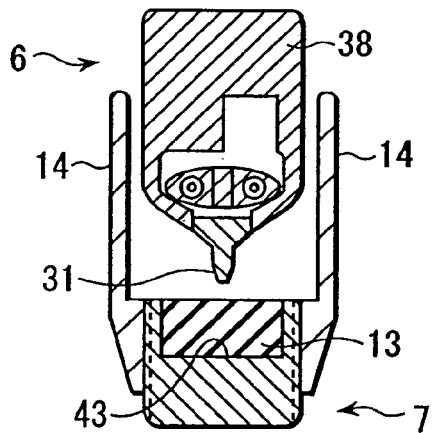
FIG. 3C is a cross sectional view of the forceps taken along the line E-E in FIG. 2A.
Figure 3D:
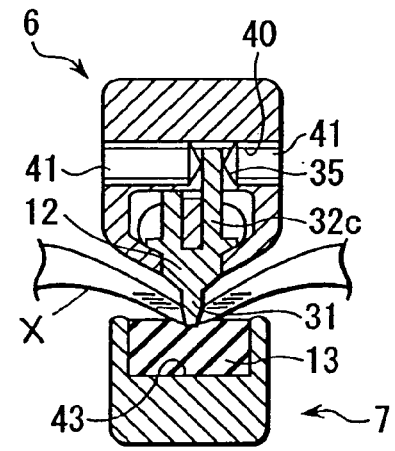
FIG. 3D is a cross sectional view of the forceps taken along the line D-D in FIG. 2A when a living tissue X is held.

Embodiments of the present invention will now be described in detail with reference to the accompanying drawings.

As can be seen in FIGS. 1A to 1D, a main body 2 of scissors-type thermal-coagulation cutting forceps 1 serving as a therapeutic device for a living tissue, include two scissor structural members 3 and 4. The scissor structural members 3 and 4 are placed one on another such that the members cross with each other substantially at the mid portion. Further, at the crossing-over portion between the scissor structural members 3 and 4, a fulcrum pin 5 is provided such as to rotatably join both scissor structural members 3 and 4 together.

At the distal end of the main body 2, a treatment portion 8 including a pair of jaws 6 and 7 serving as an openable holder portion for holding a living tissue X is provided. Further, at proximal portions of both scissors structural members 3 and 4, substantially circular finger insertion rings 9 and 10 are provided. Parts of these finger insertion rings 9 and 10 form a hand-side operation portion 11 which opens/closes a pair of jaws 6 and 7.

On a holder surface of one of the pair, jaw 6, which forms the treatment portion 8, that is, on a contact side to a living tissue X, there is provided a thin-plate heat generating plate 12 made of an excellent heat-conductivity material such as copper. On a holder surface of the other jaw 7, a saw-tooth stopper portion 13a is provided. Further, a receiving member 13, which will be explained later, is provided on the holder surface of the jaw 7. It should be noted that the stopper portion 13a is provided at the distal end side of the receiving member 13 so that it can be easily separated from the living tissue X; however it is alternatively possible that the stopper portion is provided over the entire length thereof. Further, on both side surfaces of the jaw 7, a tissue stopper 14 is formed at a proximal end side (on the fulcrum pin 5 side) so as to project towards the jaw 6. This stopper serves to prevent the living tissue X from excessively deeply entering between the pair of jaws 6 and 7 towards the proximal end side thereof.

Further, a stopper 15 is provided on one of the finger insertion rings, that is, ring 9, which forms the hand operation portion 11, and the stopper 15 projects towards the other finger insertion ring 10. This finger insertion ring 10 has a stopper receiving member 16. The stopper 15 is a screw type, and the height thereof can be adjusted depending on the screwing amount, thus making it possible to adjust the closed position of the pair of jaws 6 and 7.

Further, a groove 17 is made in one scissors structure member 3 along its longitudinal direction, and a lead line 18 is put through the groove 17. One end portion of the lead line 18 is connected to a heat generator, which will be later explained, embedded in a heat generating plate 12. The other end of the lead line 18 is connected to a connector cable 20 via a connector 19 provided in one finger insertion ring 9.

Figure 4:
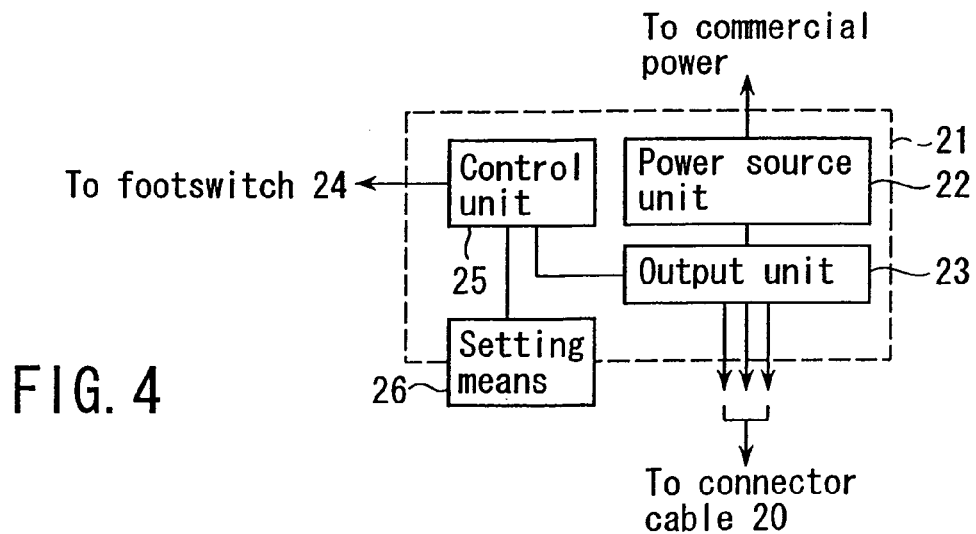
FIG. 4 is an electrical circuit diagram of a power device of this embodiment.

The connector cable 20 is connected to a power device 21 shown in FIG. 4. The power device 21 is provided with a power source unit 22 to be connected to a commercial power source, and the power source unit 22 is connected to the connector cable 20 via an output unit 23. The output unit 23 is connected to a control unit 25 to be connected to a foot switch 24, and the control unit 25 is connected to setting means 26, which sets a heat-generating temperature.

Next, the treatment portion 8 will now be described with reference to FIGS. 2A, 2B and 3A to 3D.

The heat generating plate 12 provided in one jaw 6 is a rectangular metal plate arranged in the jaw 6 in its longitudinal direction, and a projecting portion 31 of a tapered shape that narrows towards its distal end, is made on the lower side portion of the plate along its longitudinal direction.

A plurality of, in this embodiment, 3, projecting pieces 33a, 32b and 32c are provided such as to project upwards on an upper side portion of the heat generating plate 12 in its longitudinal direction at predetermined intervals. A slot is made in each of the projecting pieces 32a, 32b and 32c in its longitudinal direction, and this slot forms a heat coupling portion 33.

A through hole 34 is made in the projecting piece 32a located at the distal end side of the jaw 6 such as to go through in the lateral direction. On the projecting piece 32c located on the proximal end side of the jaw 6, a fixation plate 35 is formed integrally, such as to project upwards further than the other projecting pieces 32a and 32b.

Heat generators 36a, 36b and 36c serving as heat generating means made of thin film heat resistance elements are fixed, as being heat-coupled, onto the heat coupling portions 33 of the projecting pieces 32a, 32b and 32c, respectively in such a manner that a part of each heat generator is inserted in the slot of the respective projecting piece. These heat generators 36a, 36b and 36c are arranged at equal intervals so as to make the temperature distribution uniform, and the before-mentioned lead lines 18 are independently connected to the generators. Further, the conductive part of the tip end of the lead line 18 is covered with an insulation cover 37.

Further, a cover 38 is provided for the heat generating plate 12 so as to cover the heat coupling portions 33 of the projecting pieces 3 2a, 32b and 32c and both left and right side portions and an upper portion of each of the heat generators 36a, 36b and 36c. The cover 38 is fixed to the heat generating plate 12 at two sections, that is, the distal end side and proximal end side, of the jaw 6. The material of the cover 38 should preferably be that having a poor heat conductivity, such as stainless steel, and with such a material, the heat radiation of the heat generating plate 12 can be prevented.

More specifically, on the distal end side of the jaw 6, the cover 38 is fixed to both end portions of a fixation pin 39 put through the through hole 34 in its lateral direction. On the proximal end of the jaw 6, a screw hole 40 is made in both side surfaces of the cover 38 such as to face both side surfaces of the fixation plate 35. Fixation screws 41 are engaged respectively in the screw holes 40, and the fixation plate 35 is held as being interposed between the tip end portions of the two fixation screws 41. The distal end portion of the fixation screw 41 has a conical shape and it is brought into point contact with the fixation plate 35. In this manner, it is possible to prevent the heat of the heat generating plate 12 from propagating to the cover 38 via the fixation plate 35 and fixation screw 41.

The lower edge of the cover 38 in both right and left side edge portions abuts on the heat generating plate 12, and only the projecting portion 31 of the heat generating plate 12 is exposed from the cover 38. Further, the distal-end opening portion of the cover 38 is covered by a cap 42 pivotally fixed with the fixation pin 39.

The receiving member 13 of the jaw 7 is made of a flexible member such as rubber. The receiving member 13 is contained inside a recess portion 43 made in an upper surface of the jaw 7, and the holder surface of the receiving member 13 is made flat. The stopper portion 13a projects upwards from the holder surface of the receiving member 13. The stopper 15 is adjusted to be slightly deformable as the jaws 6 and 7 are closed together and thereby the receiving member 13 is pressed with the heat generating plate 12.

Next, the operation of the heat coagulation cut forceps 1 having the structure described above will now be described.

First, the treatment portion 8 at the distal end portion of the main body 2 is put, in a closed state, into a living tissue X containing a to-be-treated portion such as a blood vessel, not illustrated in the figure. After that, the finger insertion rings 9 and 10 of the hand-side operation unit 11 are opened, and thus the scissors structural members 3 and 4 are rotated around the fulcrum pin 5 so as to open the pair of jaws 6 and 7. In this manner, the treated portion such as a blood vessel is separated from the other part of the living tissue X, so as to expose it.

Subsequently, the separated blood vessel or the like is held between the jaws 6 and 7 in a state where the blood vessel is compressed with a relatively small and appropriate pressure suitable for the coagulation treatment. While maintaining this state, when the power device 21 is turned on, electricity is supplied to the heat generators 36a, 36b and 36c provided in the heat generating plate 12 of the jaw 7 via the connector cable 20, the connector 19 and the lead line 18. Due to the electrical resistance while applying the electricity, the heat generators 36a, 36b and 36c generate heat, and thus the treated portion such as blood vessel in the living tissue X, which is brought into contact with the surfaces of the heat generating plate 12, is coagulated and cut.

In this embodiment, 3 heat generators 36a, 36b and 36c are provided in the jaw 6, and lead lines 18 are independently connected respectively to the heat generators 36a, 36b and 36c to connect them to the power device 21. With this structure, the heat generators 36a, 36b and 36c can be controlled independently of each other to a heat generation temperature set by the setting means 26 of the power device 21.

That is, in the case where the section of the heat generating plate 12 which is in contact with the living tissue X, for example, the distal end side of the heat generator 36a lowers its calorific value, thereby decreasing the temperature at the section, the resistance value of the heat generator 36a provided on the distal end side is detected, and the output to the heat generator 36a from the output unit 23 is increased. On the other hand, in the case where the section, which is not in contact with the living tissue X, for example, the proximal end side of the heat generating plate 12, raises its calorific value, the output to the heat generator 36c on the proximal end side is decreased. With the above-described operations, an uneven temperature distribution of the heat generating plate 12 can be prevented, and the coagulation and cutting can be quickly and accurately performed.

Further, in the case where a living tissue X is to be held with a pair of jaws 6 and 7, the tissue stopper 14 projecting from the jaw 7 towards the jaw 6 side, serves to prevent the tissue X from excessively deeply entering towards the proximal end side of the pair of jaws 6 and 7.

One finger insertion ring 9, which forms the hand-side operation unit 11, is provided with the stopper 15 projecting towards the other finger insertion ring 10. With this structure, when the pair of jaws 6 and 7 is closed together, the stopper 15 abuts against the stopper receiving member 16 on the opposing side. Therefore, it is possible to confirm that the pair of jaws 6 and 7 is completely closed together, and thus the living tissue X can be cut with the pair of jaws 6 and 7 over its entire length.

It should be noted that the outer surface of the heat generating plate 12 and the outer surface of the cover 38 are coated with Teflon (registered tradename), and thus it is possible to prevent the tissue X from sticking to the surfaces.

The heat generating plate 12 should preferably be made of a material having a high heat conductivity such as copper, silver or tungsten, and the heat generators 36a, 36b and 36c may be thin film resistance heating elements, ceramic heaters, cartridge heaters, PTC heaters or the like.

Examples of the material for the receiving member 13 are rubbers (such as silicon rubber, fluorine rubber, ethylenepropylene rubber and butyl rubber), gels (including a silicon-based α-gel) and Teflon (registered tradename). Here, the saw-tooth stopper 13a may be coated with Teflon (registered tradename) for the purpose of preventing a living tissue X from sticking thereto.

Figure 5A:
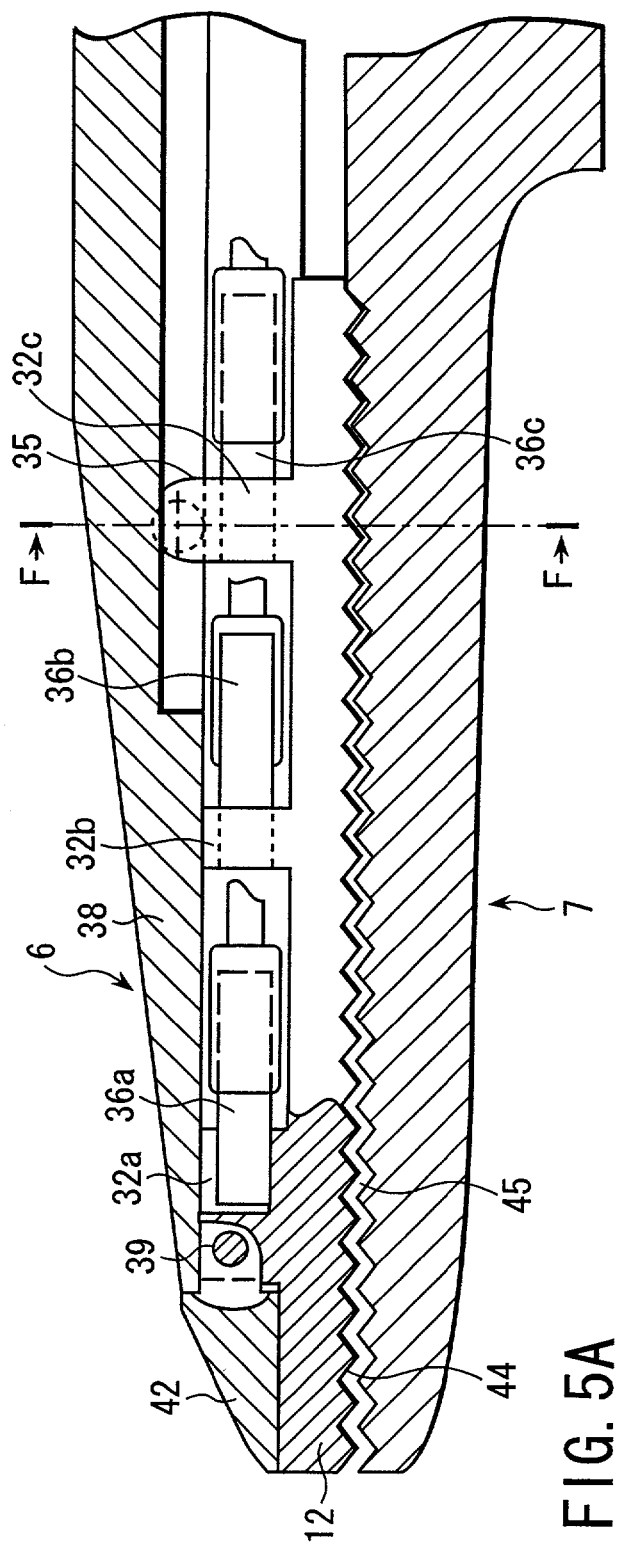
FIG. 5A is a longitudinal section view of the distal end portion of a thermal-coagulating cutting forceps according to the second embodiment of the present invention.
Figure 5B:
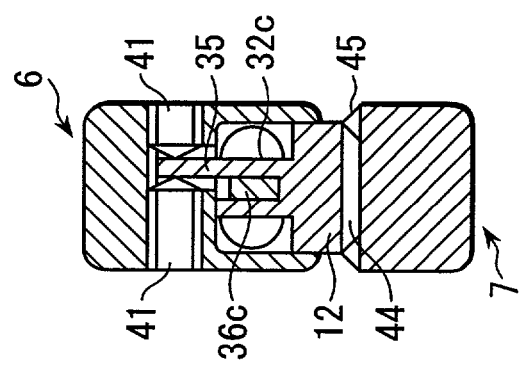
FIG. 5B is a cross section view of the forceps taken along the line F-F in FIG. 5A.

FIGS. 5A and 5B illustrate the second embodiment of the present invention. Here, the same structural elements as those of the first embodiment will be designated by the same reference numerals, and the explanations for those elements will not be repeated. In this embodiment, saw-tooth stoppers 44 and 45 are formed on the holder surface of the heat generating plate 12 of the jaw 6, and the holder surface of the jaw 7, such as to engage with each other. The holder surface of the heat generating plate 12 is formed into a wide flat surface, which is a structure suitable for coagulation, and otherwise the second embodiment is similar to the first embodiment.

FIGS. 6A to 6C illustrate the third embodiment of the present invention. Here, the same structural elements as those of the first embodiment will be designated by the same reference numerals, and the explanations for those elements will not be repeated.

In this embodiment, a plurality of, in this embodiment, 3, projecting pieces 46a, 46b and 46c are provided on an upper side portion of the heat generating plate 12 at predetermined intervals in its longitudinal direction and in a zigzag manner when viewed from top, such as to project upwards on an upper side portion of the heat generating plate 12 in its longitudinal direction at predetermined intervals. A slot is made in each of the projecting pieces 46a, 46b and 46c in its longitudinal direction, and this slot forms a heat coupling portion 47.

At each heat coupling portion 47, a part of each of the heat generators 36a, 36b and 36c is inserted in the respective slot, to be fixed therein while being heat-coupled. To these heat generators 36a, 36b and 36c, the above-described lead lines 18 are independently connected. Further, the conductive portion of the distal end portion of each lead line 18 is covered with the insulation cover 37.

In this embodiment, a slit is made in each of the projecting pieces 46a, 46b and 46c in its lateral direction, and each slot forms a respective heat coupling portion 47. With this structure, the thickness of the jaw 6 can be reduced in its up-and-down direction. Further, the heat generators 36a, 36b and 36c are offset in the width direction of the jaw 6, and therefore there is such an advantage that the wiring of the lead lines 18 can be easily performed.

Figure 7A:
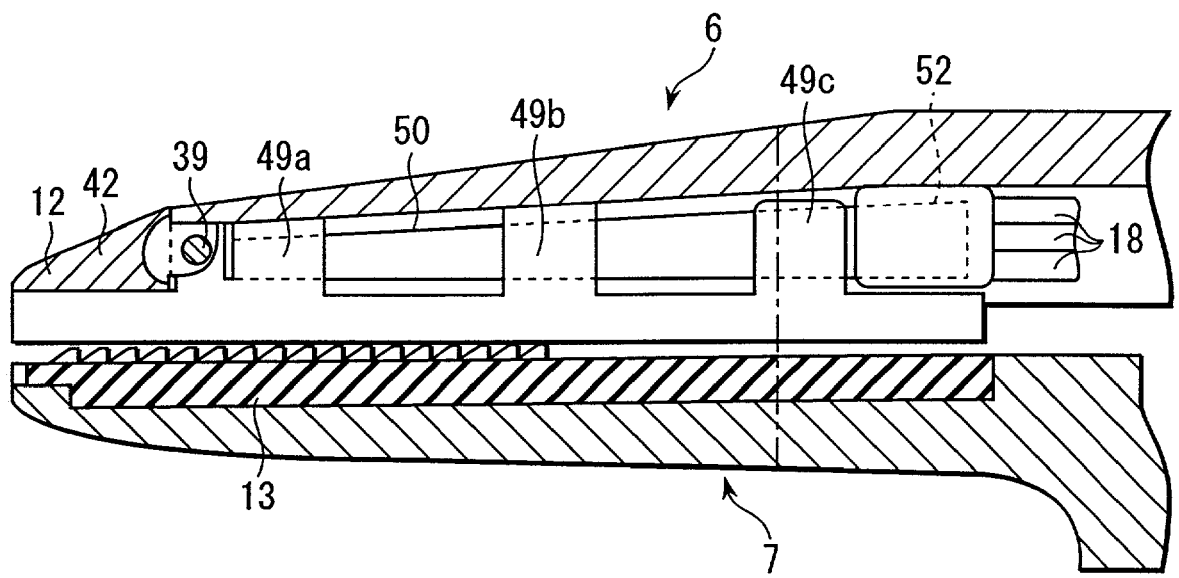
FIG. 7A is a longitudinal section view of the distal end portion of a thermal-coagulating cutting forceps according to the fourth embodiment of the present invention.
Figure 7B:
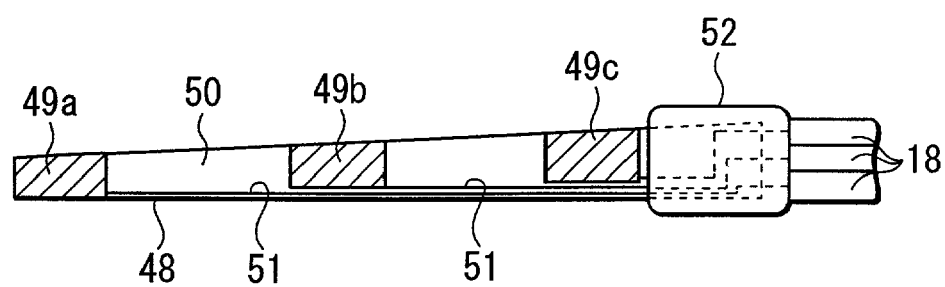
FIG. 7B is a side view of a heat generating unit.

FIGS. 7A and 7B illustrate the fourth embodiment. Here, the same structural elements as those of the first embodiment will be designated by the same reference numerals, and the explanations for those elements will not be repeated.

In this embodiment, a heat generating substrate 48 is provided on an upper surface of the heat generating plate 12. A heat generating member 50 having a tapered shape whose width gradually narrows towards its distal end is provided on the heat generating substrate 48. On the heat generating member 50, a plurality of, in this embodiment, 3, heat generating portions 49a, 49b and 49c are independently provided to be apart from each other in its longitudinal direction. These heat generating portions 49a, 49b and 49c are formed in accordance with the width of the heat generating substrate 48 such that the heat generating portion 49a on the distal end side has the smallest width, and the portion 49c on the proximal end side has the largest width. These heat generating portions 49a, 49b and 49c are electrically connected to switch circuits 51 of the heat generating substrate 48 independently of each other. The switch circuits 51 are electrically connected to lead lines 18 on the proximal end side of the heat generating substrate 48, and the connection portion is covered with an insulating cover 52.

According to this embodiment, the structure of the heat generating member 50 is simplified. Further, the heat generating portions 49a, 49b and 49c are formed in accordance with the width of the heat generating substrate 48 such that the heat generating portion 49a on the distal end side has the smallest width and the portion 49c on the proximal end side has the largest width. With this structure, the thickness of the jaw 6 in the up-and-down direction can be reduced. Further, the connection of the lead lines 18 can be conducted at one place, making it easy to carry out wiring. In addition, since the heat generating member 50 is made in the form of a unit, when some repair is needed, it suffices if the heat generating member unit is replaced with a new one.

Figure 8A:
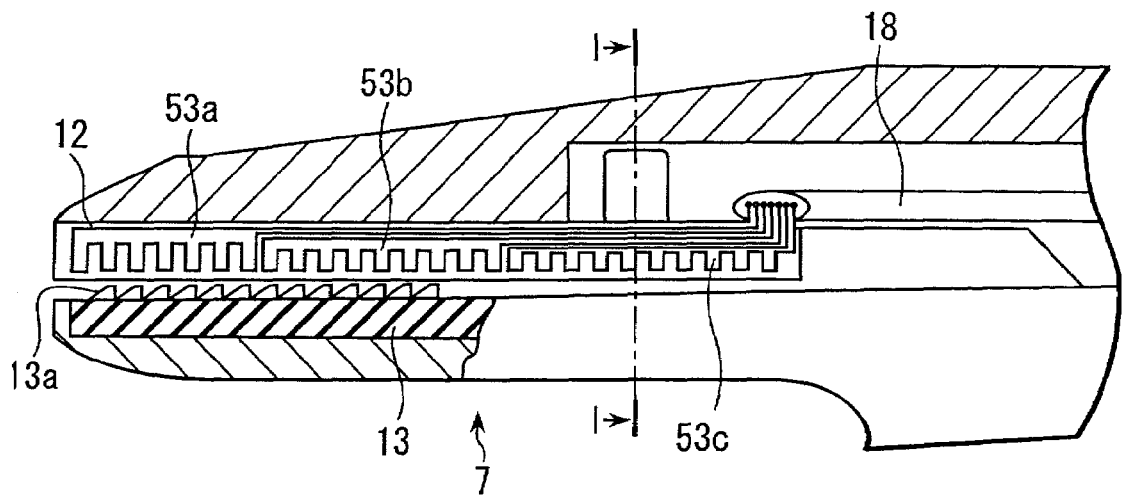
FIG. 8A is a longitudinal section view of the distal end portion of a thermal-coagulating cutting forceps according to the fifth embodiment of the present invention.
Figure 8B:
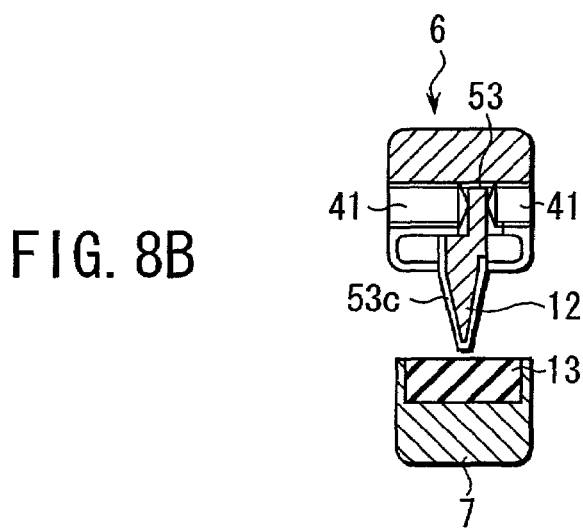
FIG. 8B is a cross sectional view of the forceps taken along the line I-I in FIG. 8A.
Figure 8C:
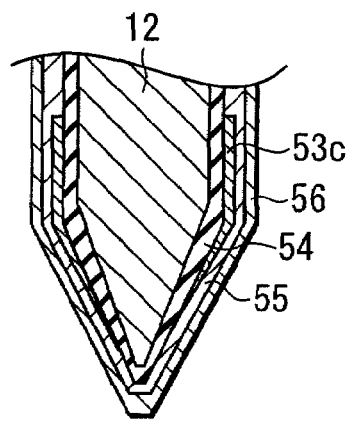
FIG. 8C is an enlarged cross section view of a heat generating plate of the same embodiment.

FIGS. 8A to 8C illustrate the fifth embodiment. Here, the same structural elements as those of the first embodiment will be designated by the same reference numerals, and the explanations for those elements will not be repeated. In this embodiment, a heat generating plate 12 is formed to have a tapered shape whose width gradually narrows towards its lower end edge. On both side surfaces of the heat generating plate 12, thin film resistance heat elements 53a, 53b and 53c are provided to be apart from each other in its longitudinal direction of the jaw 6. These thin film resistance heat elements 53a, 53b and 53c are electrically connected to lead lines 18 in the proximal end side of the jaw 6.

Each of the thin film resistance heat elements 53a, 53b and 53c is formed on both side surfaces of the heat generating plate 12 to have a three-layer structure in which a insulation layer 54, a resistance member 55 and a Teflon-coating layer 56 (Teflon: registered tradename) are formed in the order.

According to this embodiment, the connection of the lead lines 18 can be conducted at one place, making it easy to carry out wiring. In addition, since the thin film resistance heat elements 53a, 53b and 53c are integrated with the heat generating plate 12, when some repair is needed, it suffices if the heat generating plate 12 is replaced with a new one. Alternatively, the elements may be of, not only the thin film resistance type (which can be produced by the semiconductor technique), but also the thick film resistance (which can be produced by the print method, plating method or the like).

Figure 9:
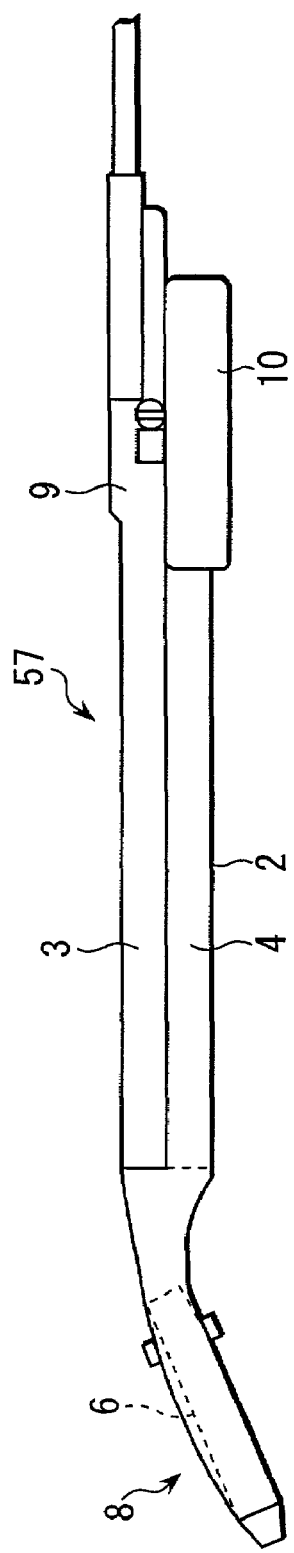
FIG. 9 is a plan view of a thermal-coagulating cutting forceps according to the sixth embodiment of the present invention.

FIG. 9 illustrates the sixth embodiment, and the same structural elements as those of the first embodiment are designated by the same reference numerals. In this embodiment, a pair of jaws 6 and 7 which forms a treatment unit 8 is bent to the left side with reference to the axial line of the main body 2. However, for simplifying the structure, the heat generating plate 12 and the cover 38 are made to have a straight-line shape. (Note that a broken line indicates the cover.) In this embodiment, when a living tissue X is to be held with the jaws 6 and 7, the operator can easily observe how the tissue is being held. In this manner, the living tissue X can be held easily. Thus, with this embodiment, the usability of the forceps can be improved.

Figure 10:
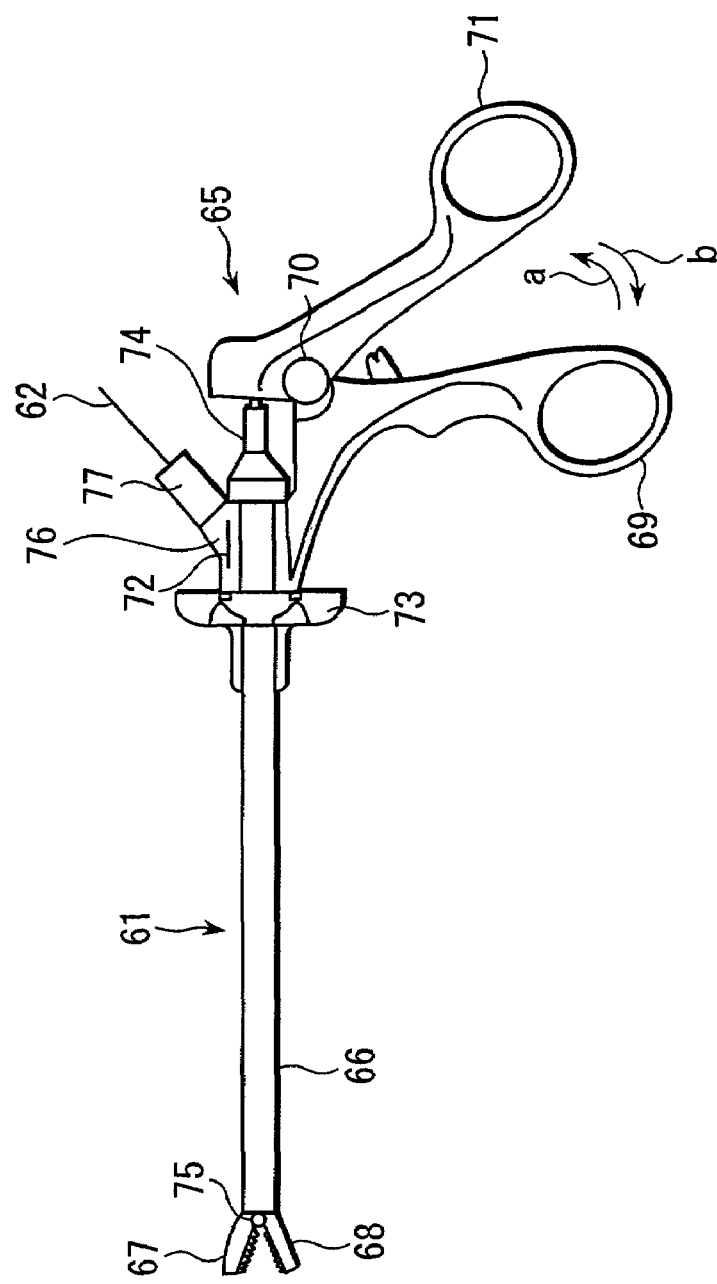
FIG. 10 is a side view of a thermal-coagulating cutting forceps used for an endoscopic operation according to the seventh embodiment of the present invention.

FIG. 10 illustrates the seventh embodiment, and is a side view of thermal-coagulation cutting forceps used for endoscopic operations. The thermal coagulation cutting forceps 61, which serves as a therapeutic device for living tissues, are connected to a power device (not shown) via a connector table 62. The thermal-coagulation cutting forceps 61 is made of a hand-side operation portion 65 serving as holding portion driving means, an insertion portion 66 and a pair of holding portions 67 and 68 provided at a distal end of the insertion portion 66.

The hand-side operation portion 65 includes an operation portion main body 72, a fixation handle 69 provided to be integral with the operation portion main body 72, and a movable handle 71 provided rotatably on the main body 72 around a pivotal axis 72 serving as the fulcrum. An insertion portion 66 is provided on the operation portion main body 72 such as to be rotatable around the axial center by a rotating portion 73.

The insertion portion 66 is made of a small-diameter pipe, to which a drive axis 74 is inserted such as to be able to advance or retract in the axial direction. The proximal end portion of the drive axis 7 is coupled with the movable handle 7, and the distal end portion thereof is provided with a pair of holding portions 67 and 68. The holding portions 67 and 68 are formed openable/closable around a pivotal pin 75 serving as the fulcrum. When the movable handle 71 is rotated in the direction indicated by an arrow a, the drive axis 74 retracts and thus a pair of holding portions 67 and 68 are closed. On the other hand, when rotated in the direction b, the drive axis 74 advances and thus a pair of holding portions 67 and 68 is opened.

Further, a connector portion 76 is provided for the operation portion main body 72 and a connector 77 of the connector cable 62 can be detachably connected to the connector portion 76. The connector portion 76 is electrically connected to a heat generating member (not shown) provided in the holder portion 67 along the drive axis 74.

With this structure, when the hand-side operation portion 65 is held and the movable handle 71 is rotated in the direction indicated by an arrow b with respect to a fixed handle 69, the drive axis 74 advances and thus the holder portions 67 and 68 are opened. While maintaining this state, the thermal coagulation cutting forceps 61 are advanced so as to interpose the section of the living tissue X that needs to be coagulated and cut, between the holder portions 67 and 68. Then, when the movable handle 71 is rotated in the direction indicated by an arrow a, the drive axis 74 retracts and thus the holding portions 67 and 68 are closed. In this manner, the living tissue X can be coagulated and cut in the similar manner to that of the first embodiment.

Figure 11A:
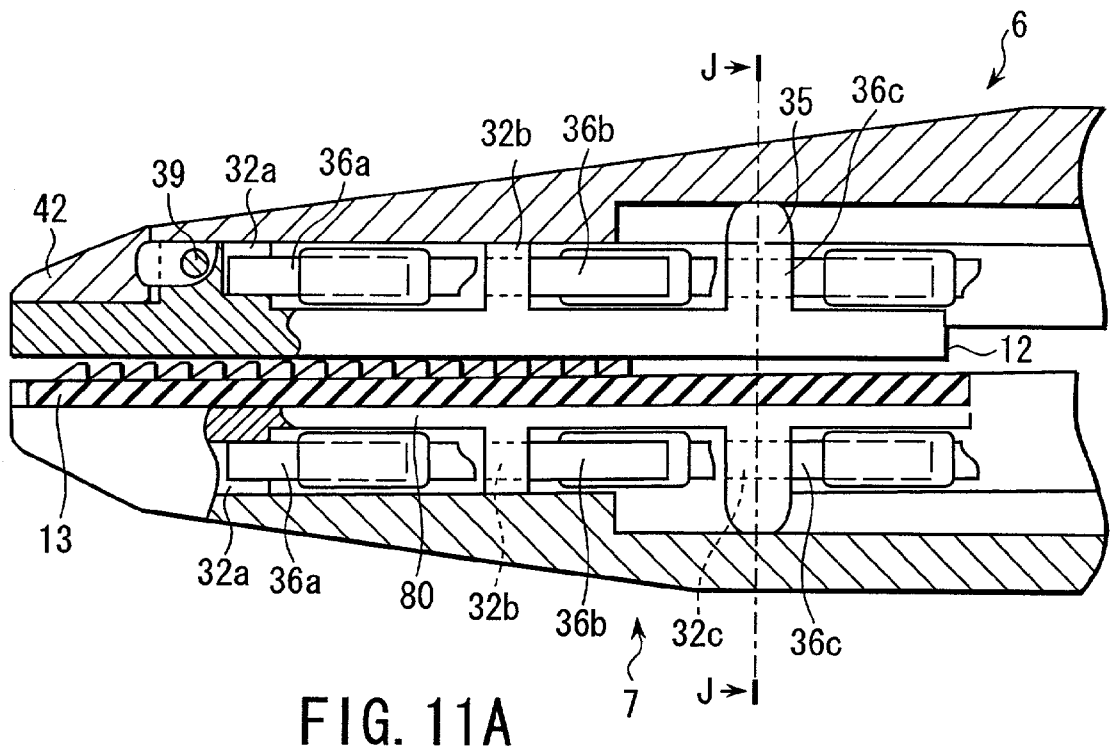
FIG. 11A is a longitudinal section view of the distal end portion of a thermal-coagulating cutting forceps according to the eighth embodiment of the present invention.
Figure 11B:
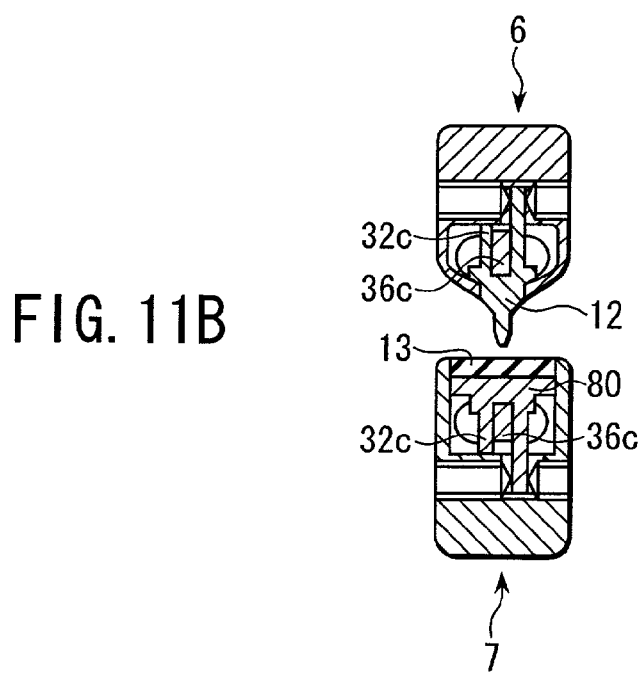
FIG. 11B is a cross sectional view of the forceps taken along the line J-J in FIG. 11A.
Figure 13A:
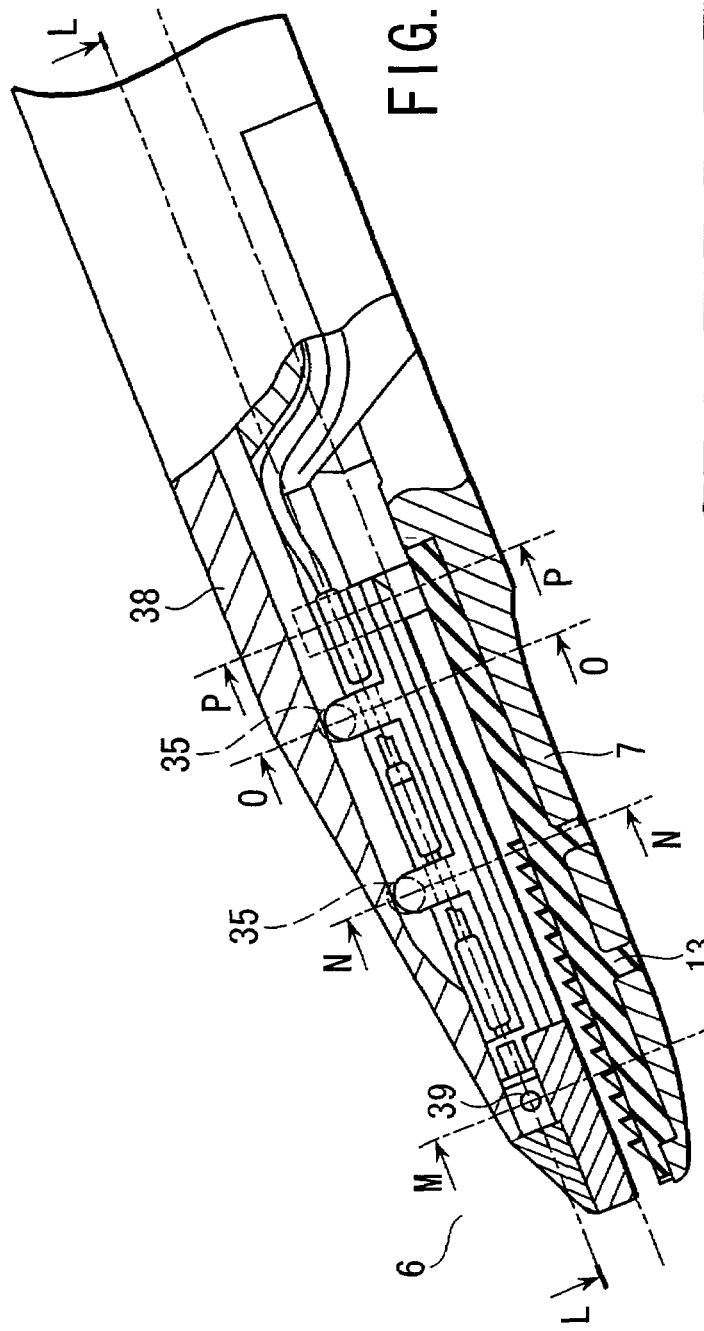
FIG. 13A is a cross sectional view of the device of this embodiment taken along the line K-K in FIG. 13B.
Figure 13B:
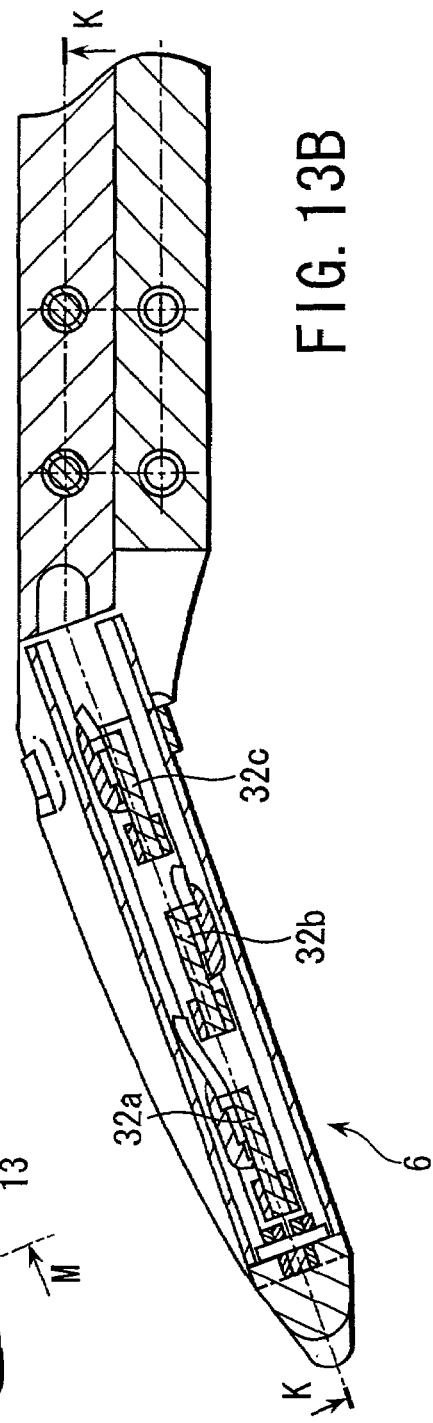
FIG. 13B is a cross sectional view taken along the line L-L in FIG. 13A.

FIGS. 11A and 11B illustrate the eighth embodiment of the present invention. Here, the same structural elements as those of the first embodiment will be designated by the same reference numerals, and the explanations for those elements will not be repeated. In this embodiment, heat generating means is provided for both of a pair of jaws 6 and 7. In the jaw 7, a heat generating plate 80 is provided on a lower side of the receiving member 13 having a flexibility, and further heat generating members 36a, 36b and 36c are provided for the heat generating plate 80 in a similar structure to that of the first embodiment.

In this embodiment, a living tissue X is held with a pair of jaws 6 and 7 and then subjected to coagulation and cutting. During this operation, the living tissue X can be heated from both side surfaces that are holding the tissue, and therefore the efficiency of the coagulation and cutting can be further improved, thereby making it possible to shorten the time required for operations.

FIGS. 12A to 14D illustrate the ninth embodiment of the present invention. Here, the same structural elements as those of the first embodiment will be designated by the same reference numerals, and the explanations for those elements will not be repeated.

In this embodiment, thermal coagulation cutting forceps 100 are provided at approximately the mid position of the scissors structural member 3 in its longitudinal direction to project towards the scissors structural member 4, in consideration of the strength of the stopper 15. Further, the connector cable 20 is fixed to a bent stopper portion 101, and thus it is electrically connected to the power via a connector not shown in the figure. Further, the fulcrum pin 5 is formed to have a small head portion so that it does not project much from the scissors structural members 3 and 4. The finger insertion rings 9 and 10 are formed separate from the scissors structural members 3 and 4 and fixed thereto with at least two screws. In addition, as can be seen in FIGS. 12B and 12C, the jaws 6 and 7 are formed such that the hand-side section of the jaws do not create a large step or gap when they are closed.

Figure 14A:
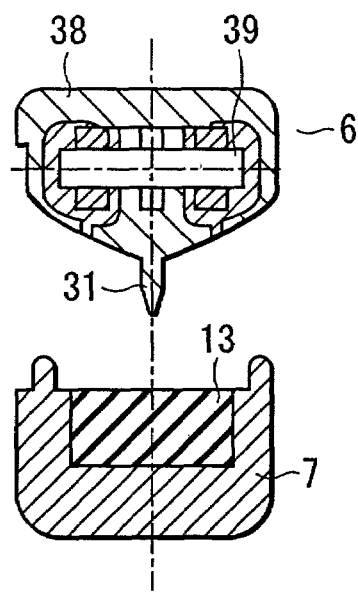
FIG. 14A is a cross sectional view of the device of this embodiment taken along the line M-M in FIG. 13A.
Figure 14B:
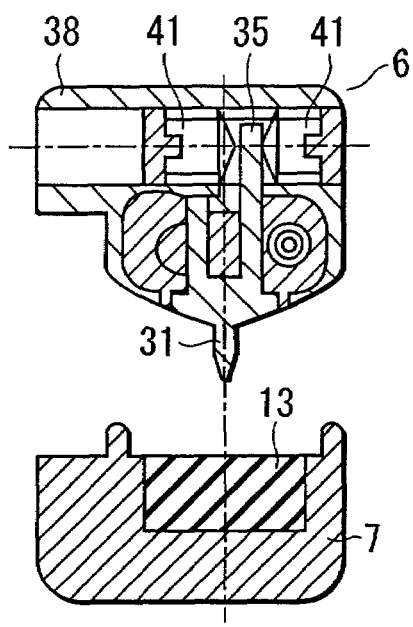
FIG. 14B is a cross sectional view taken along the line N-N in FIG. 14B.
Figure 14C:
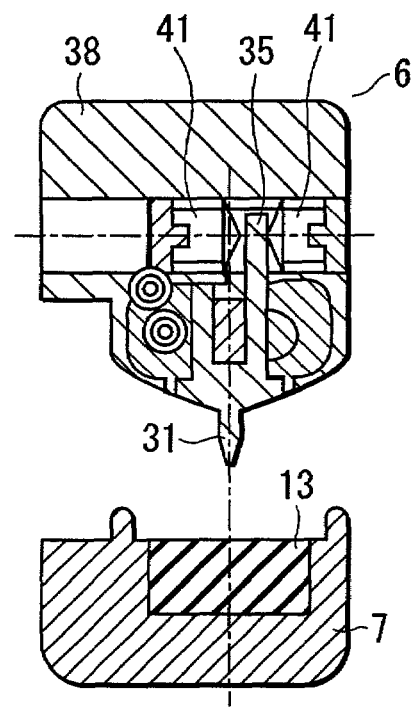
FIG. 14C is a cross sectional view taken along the line O-O in FIG. 13A.
Figure 14D:
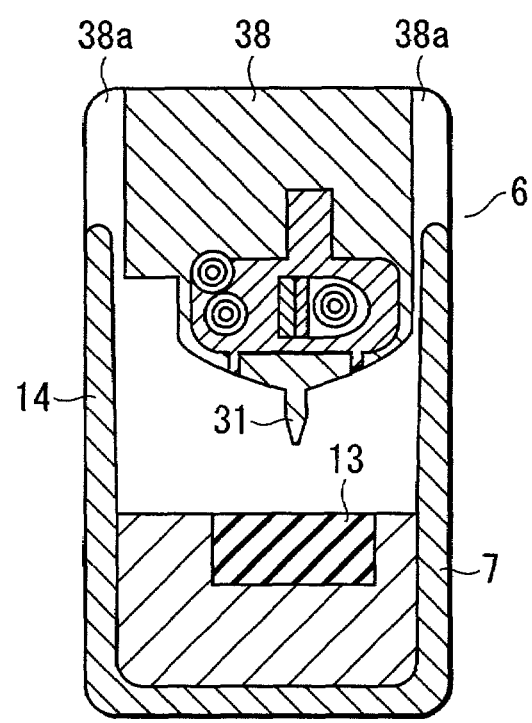
FIG. 14D is a cross sectional view taken along the line P-P in FIG. 13A.

Further, as shown in FIGS. 14A to 14D, the receiving member 13 is formed with a rubber lining. As shown in FIGS. 14B and 14C, a fixation plate 35 is integrally made with the projecting pieces 32b and 32c formed on the jaw 7, such as to project upwards. A fixation screw 41 is engaged with a screw hole 40 that opposes the fixation plate 35, and the fixation plate 35 is fixed as it is interposed between the distal end portions of the two fixation screws 41. More specifically, the cover 38 is fixed by a plurality of points so as to assure the fixation. Further, as shown in FIG. 14D, a tissue stopper 14 is formed of one part in order to simplify its structure, and a recess groove 38a is made in the cover 38 to guide the tissue stopper 14.

Figure 15:
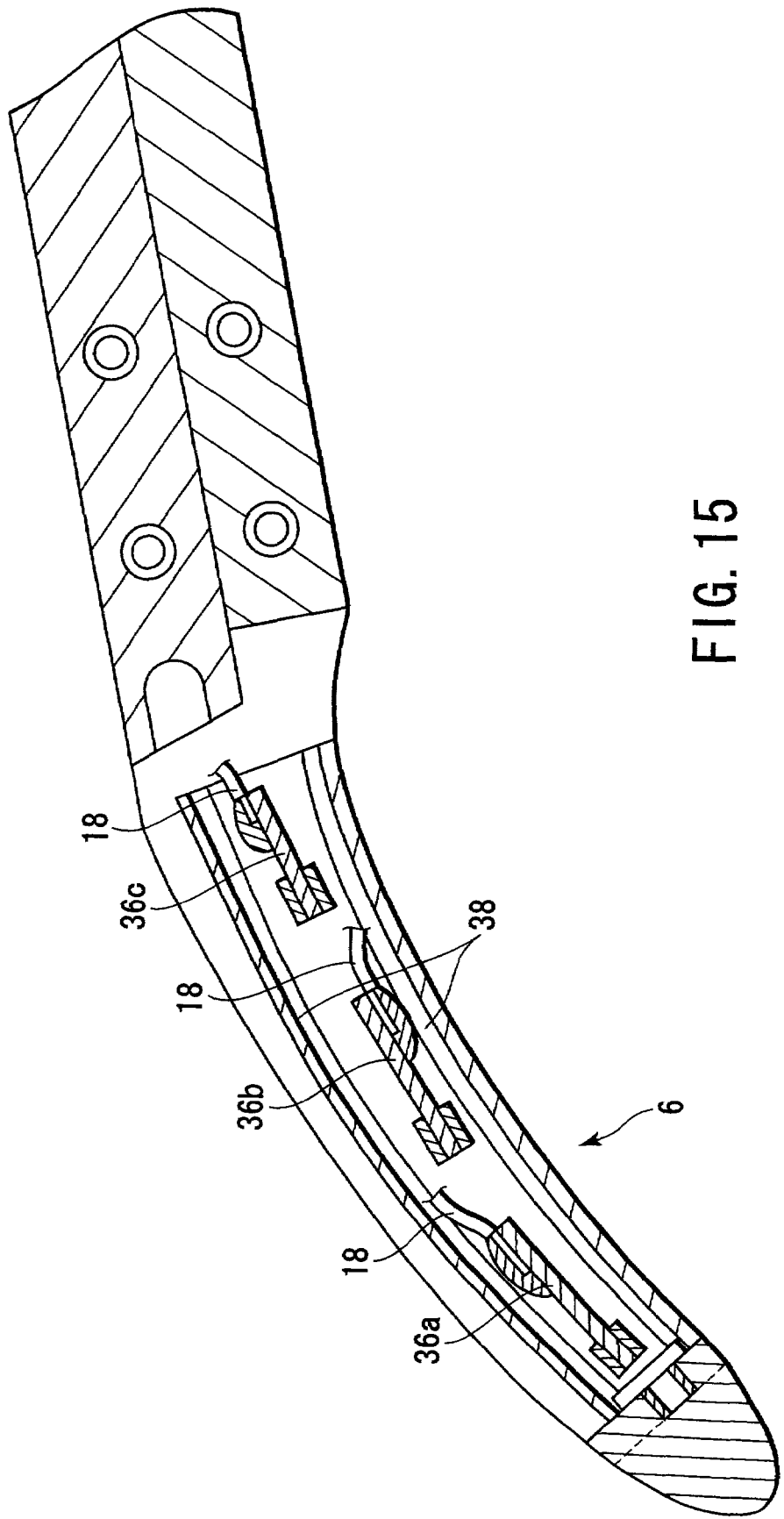
FIG. 15 is a longitudinal section view of a thermal-coagulating cutting forceps according to the tenth embodiment of the present invention.

FIG. 15 illustrates the tenth embodiment of the present invention. Here, the same structural elements as those of the first embodiment will be designated by the same reference numerals, and the explanations for those elements will not be repeated. In this embodiment, jaws 6 and 7, which form a treatment portion 8, are bent in an arc-shaped manner as viewed horizontally, and heat generating members 36a, 36b and 36c are provided on the jaws 6 and 7 along their arc shape. The heat generating members 36a, 36b and 36c are independently connected to lead lines 18. Further, a cover 38 that covers both left and right side portions and upper portion of the heat generating members 36a, 36b and 36c is also bent to meet with the bent shape of the jaws 6 and 7.

It should be noted that, in the above-described embodiments, three heat generating members are arranged on a jaw to be apart from each other in its longitudinal direction; however the number of heat generating members is not limited to this.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A therapeutic device for treating a living tissue, comprising:
   a pair of openable/closable elongate holding portions relatively rotatable about a lateral axis, the holding portions being configured to hold the living tissue therebetween, each having proximal and distal ends, and extending in a lengthwise direction normal to the lateral axis;
   an elongate heating portion provided for at least one of the holding portions and configured to treat the living tissue, the heating portion extending in the lengthwise direction between the proximal and distal ends of the holding portion, the heating portion having an elongate treatment surface which is contacted with the living tissue along the lengthwise direction; and
   a plurality of heat generators arranged in the heating portion in the lengthwise direction, such that each heat generator of the plurality of heat generators is independently controllable to maintain a desired temperature profile along the lengthwise direction for the treatment surface of said heating portion, by generating heat and transmitting the heat to the living tissue through the treatment surface, the heating portion being electrically insulated from the heat generators.

2. The therapeutic device according to claim 1, wherein said plurality of heat generators are heating members independent of each other.

3. The therapeutic device according to claim 2, wherein the heating portion extends along the holding portion, and said heating members are arranged along the lengthwise direction of the heating portion and are respectively connected to electric lead lines to be independently controllable.

4. The therapeutic device according to claim 3, wherein the heating members are separated from each other, and positioned between the holding portion and the heating portion.

5. The therapeutic device according to claim 1, wherein said plurality of heat generators comprise a single heat generating member having a plurality of heating areas independent of each other.

6. The therapeutic device according to claim 5, wherein said heating areas of the heat generating member are arranged along an extending direction of the heating portion and are respectively connected to electric lead lines to be independently controllable.

7. The therapeutic device according to claim 6, wherein the heat generating member is positioned between the holding portion and the heating portion.

8. A system comprising the therapeutic device according to claim 5, a power device, and a plurality of lead lines for electrically connecting the heat generators to the power device, so that the power device provides different power outputs to the respective areas of the heating portion.

9. The system according to claim 8, in which the power device includes a setting member which independently sets said plurality of heat generators to heat generation temperatures.

10. The system according to claim 8, in which the power device provides different power outputs to the heat generators according to the temperatures of the respective areas of the heating portion.

11. The therapeutic device according to claim 1, wherein said plurality of heat generators are thin film resistance heating elements.

12. The therapeutic device according to claim 1, wherein said plurality of heat generators are thick film resistance heating elements.

13. The therapeutic device according to claim 1, wherein said plurality of heat generators are ceramic heaters.

14. The therapeutic device according to claim 1, wherein said plurality of heat generators are PTC heaters.

15. The therapeutic device according to claim 1, wherein said plurality of heat generators are cartridge heaters.

16. The therapeutic device according to claim 1, wherein two heating portions are respectively provided on the holding portions to face each other.

17. The therapeutic device according to claim 1, in which said plurality of heat generators are formed integrally with the heating portion.

18. The therapeutic device according to claim 1, wherein the plurality of heat generators is operable to maintain the desired temperature for the entire treatment surface of said heating portion.

19. The system according to claim 1, wherein the elongate treatment surface of the heating portion is configured to contact the living tissue without a contact portion present between the contact portions in the lengthwise direction.

20. The system according to claim 19, wherein the treatment surface is a contiguous flat surface.

21. The system according to claim 19, wherein the treatment surface is a contiguous saw-tooth surface.

22. The system according to claim 1, further including a lead line configured to electrically connect an electric source and each of the heat generators, each of the heat generators including a sensor for detecting a condition of the heat generator to control the electric source.

23. The system according to claim 22, where each of the heat generators is formed of a thin film heat resistance element so that the heat resistance element heats the heating portion by a current from the electric source; and
   the sensor detects a variation of a resistance of the heat resistance element.

24. The system according to claim 1, wherein said heat generators are arranged in the lengthwise direction and in a zigzag manner in a plane parallel to the treatment surface.

* * * * *